US006010532A

United States Patent [19]

Kroll et al.

[11] Patent Number: 6,010,532
[45] Date of Patent: Jan. 4, 2000

[54] DUAL PATH IMPLANTABLE HEARING ASSISTANCE DEVICE

[75] Inventors: Kai Kroll, Minnetonka; Joel A. Kennedy, Arden Hills, both of Minn.

[73] Assignee: St. Croix Medical, Inc., Minneapolis, Minn.

[21] Appl. No.: 08/755,180

[22] Filed: Nov. 25, 1996

[51] Int. Cl.[7] .......... A61F 2/18
[52] U.S. Cl. .......... 623/10
[58] Field of Search .......... 623/10

[56] References Cited

U.S. PATENT DOCUMENTS

| | | | |
|---|---|---|---|
| 3,557,775 | 1/1971 | Mahoney . | |
| 3,594,514 | 7/1971 | Wingrove . | |
| 3,712,962 | 1/1973 | Epley . | |
| 3,764,748 | 10/1973 | Branch et al. . | |
| 3,931,648 | 1/1976 | Shea, Jr. . | |
| 4,150,262 | 4/1979 | Ono | 179/107 BC |
| 4,606,329 | 8/1986 | Hough | 128/1 R |
| 4,612,915 | 9/1986 | Hough et al. | 128/1 R |
| 4,729,366 | 3/1988 | Schaefer et al. | 128/1.6 |
| 4,774,933 | 10/1988 | Hough et al. . | |
| 4,776,322 | 10/1988 | Hough et al. . | |
| 4,817,607 | 4/1989 | Tatge . | |
| 4,840,178 | 6/1989 | Heide et al. . | |
| 4,850,962 | 7/1989 | Schaefer | 600/25 |
| 4,957,478 | 9/1990 | Maniglia . | |
| 5,012,520 | 4/1991 | Steeger . | |
| 5,015,224 | 5/1991 | Maniglia . | |
| 5,015,225 | 5/1991 | Hough et al. . | |
| 5,163,957 | 11/1992 | Sade et al. . | |
| 5,277,694 | 1/1994 | Leysieffer et al. . | |
| 5,282,858 | 2/1994 | Bisch et al. . | |
| 5,338,287 | 8/1994 | Miller et al. . | |
| 5,360,388 | 11/1994 | Spindel et al. . | |
| 5,411,467 | 5/1995 | Hortmann et al. . | |
| 5,456,654 | 10/1995 | Ball . | |
| 5,498,226 | 3/1996 | Lenkauskas . | |
| 5,531,787 | 7/1996 | Lesinski et al. . | |
| 5,554,096 | 9/1996 | Ball . | |
| 5,571,148 | 11/1996 | Loeb et al. . | |
| 5,603,726 | 2/1997 | Schulman et al. . | |
| 5,624,376 | 4/1997 | Ball et al. . | |
| 5,800,336 | 9/1998 | Ball et al. . | |

OTHER PUBLICATIONS

"Issues and Answers —The Nucleus 22 Channel Cochlear Implant System", Product Brochure published by Cochlear Corporation, 34 pp. (1995).
Staller, S.J., "Cochlear Implants: A Changing Technology", *The Hearing Journal,* vol. 49, No. 3, pp. 10, 58–60, 62, 64 (Mar. 1996).
Staller, S.J., "Cochlear Implants: A Changing Technology," The Hearing Journal, 49(3):10, 58–60, 62, 64,(1996).
"Issuses and Answers —The Nucleus 22 Channel Cochlear Implant System," product brochure published by Cochlear Corp., 1–34, (1995).
Spindel, PhD., J.H., et al., "The Round Window Electromagnetic Implantable Hearing Aid Approach," Otolaryngologic Clinics of North America, 28;189–206. (1995).
"Middle Ear Implant: Implantable Hearing Aids," Advances in Audiology, vol. 4, M. Hoke Series Editor, Karger, 1–169, (1988).

*Primary Examiner*—Michael J. Milano
*Attorney, Agent, or Firm*—Patterson & Keough, P.A.

[57] ABSTRACT

A dual path implantable hearing assistance system transduces sound vibrations of the malleus in one or both ears into electrical signals, processes the electrical signals to provide one or more resulting output electrical signals, and transduces the output signals into mechanical vibrations provided to the stapes in one or both ears. Communication between an electronics device and at least one ear is either wireless or through subcutaneous lead wires. The system may have two input paths and two output paths, programmable to provide the function of two separate single path systems, but capable of combining the signals such as by weighted summing. The system may have also have two input paths and one output path; or, one input path and two output paths; or, one input path and one output path, each associated with a different ear.

22 Claims, 6 Drawing Sheets

DUAL PATH IMPLANTABLE HEARING ASSISTANCE DEVICE

THE FIELD OF THE INVENTION

This invention relates to an electromechanical hearing assistance device for use in an at least partially implantable middle ear hearing system.

BACKGROUND

In some types of partial middle ear implantable (P-MEI) or total middle ear implantable (T-MEI) hearing aid systems, sounds produce mechanical vibrations which are transduced by an electromechanical input transducer into electrical signals. These electrical signals are in turn provided to a device which amplifies the signal and provides it to an electromechanical output transducer. The electromechanical output transducer vibrates an ossicular bone in response to the applied amplified electrical signals, thus improving hearing.

A typical single path electronic hearing assistance system for amplifying signals received from an input transducer has a single input path for receiving the signal, circuitry to produce the desired output electrical signal, and a single output path for providing the output signal to an output transducer. Such devices are useful for assisting hearing in only one ear. If a person requires assistance in both ears, two devices must be used, one for each ear.

SUMMARY

The invention provides an at least partially middle ear implantable dual path electronic hearing assist system and method of use in both of a person's ears. The invention includes components for implantation within the middle ear regions of each ear, and provides: dual input paths; or, dual output paths; or, both dual input paths and dual output paths; or, a single input path corresponding to a first ear and a single output path corresponding to a second ear. The system is capable of use as a partial middle ear implantable (P-MEI) hearing aid system or a total middle ear implantable (T-MEI) hearing aid system.

In one embodiment, the invention simulates two single path devices. Each middle ear has an implanted input transducer and an implanted output transducer. Each input transducer transduces mechanical sound vibrations into electrical signals that are separately provided to a dual path device. The device processes the received electrical signals and provides a resulting output electrical signals to drive each output transducer and produce mechanical output vibrations, such as to the stapes in each middle ear.

In another embodiment, each middle ear has an input transducer for transducing mechanical sound vibrations into electrical signals that are separately provided to the device. The device processes the received electrical signals and provides a single resulting electrical output signal to one output transducer in one middle ear. The output transducer transduces the electrical output signal into mechanical output vibrations in the middle ear in which the output transducer is disposed.

In another embodiment, each middle ear has an output transducer for receiving output electrical signals from the device that are transduced into mechanical output vibrations. Only a single input transducer is used, disposed within one of the middle ears for receiving mechanical sound vibrations that are transduced into an electrical signal provided to the device.

In another embodiment, a first middle ear has an input transducer for transducing received mechanical sound vibrations into an electrical input signal provided to the device. The device processes the received electrical input signal and provides an output electrical signal to an output transducer disposed within a second middle ear. The output transducer in the second middle ear transduces the received electrical signal into mechanical output vibrations in the second middle ear.

Thus, the invention uses only one electronic device for providing various types and combinations of hearing assistance in both ears of a hearing impaired person.

BRIEF DESCRIPTION OF THE DRAWINGS

In the drawings, like numerals describe substantially similar components throughout the several views.

DETAILED DESCRIPTION

Figure 1:
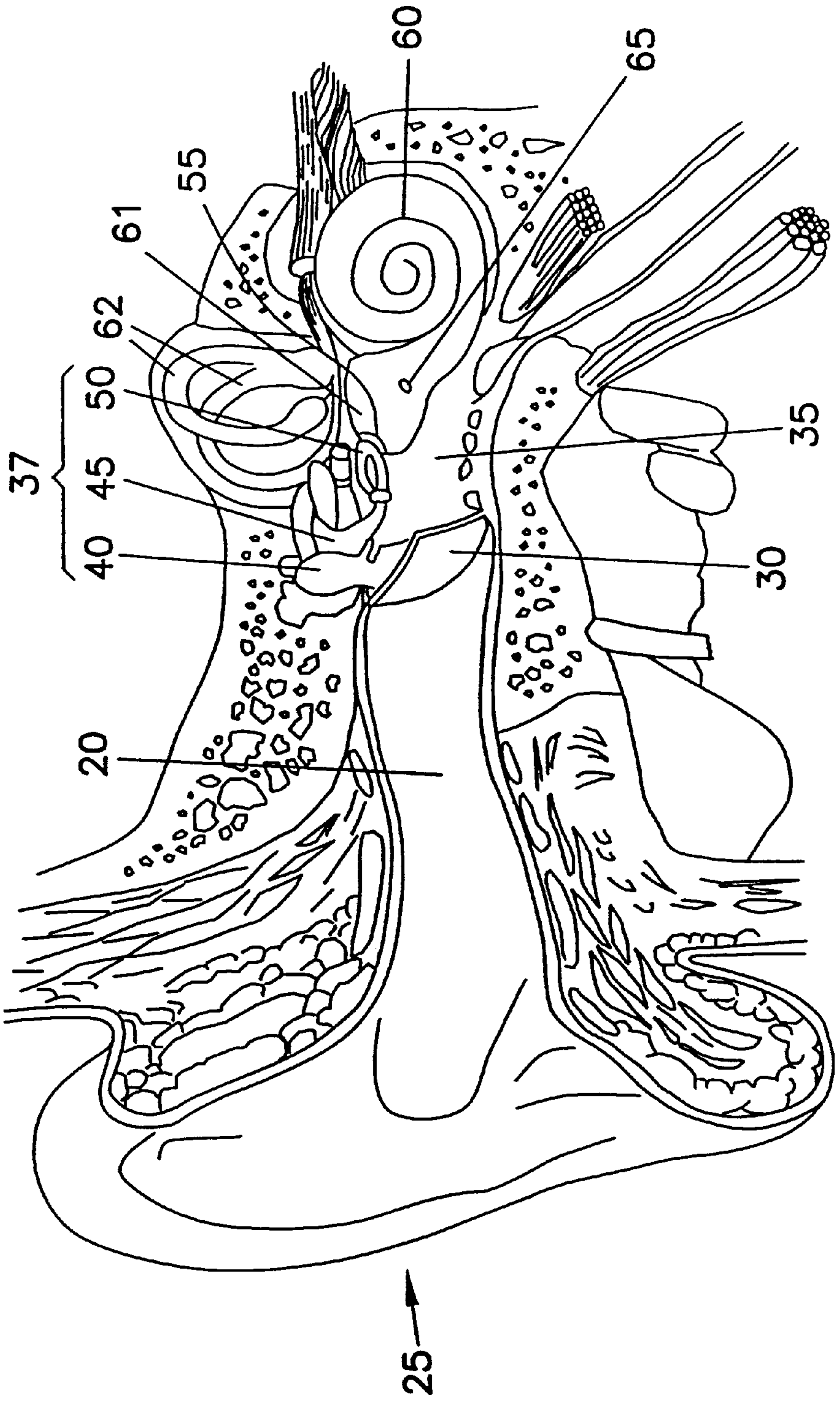
FIG. 1 illustrates a frontal section of an anatomically normal human ear in which the invention operates.

The invention provides an electronic device which is particularly advantageous when used in a middle ear implantable hearing aid system such as a partial middle ear implantable (P-MEI), total middle ear implantable (T-MEI), or other hearing aid system. A P-MEI or T-MEI hearing aid system assists the human auditory system in converting acoustic energy contained within sound waves into electrochemical signals delivered to the brain and interpreted as sound. FIG. 1 illustrates generally a human auditory system. Sound waves are directed into an external auditory canal 20 by an outer ear (pinna) 25. The frequency characteristics of the sound waves are slightly modified by the resonant characteristics of the external auditory canal 20. These sound waves impinge upon the tympanic membrane (eardrum) 30, interposed at the terminus of the external auditory canal 20, between it and the tympanic cavity (middle ear) 35. Variations in the sound waves produce tympanic vibrations. The mechanical energy of the tympanic vibrations is communicated to the inner ear, comprising cochlea 60, vestibule 61, and semicircular canals 62, by a sequence of articulating bones located in the middle ear 35. This sequence of articulating bones is referred to generally as the ossicular chain 37. Thus, the tympanic membrane 30 and ossicular chain 37 transform acoustic energy in the external auditory canal 20 to mechanical energy at the cochlea 60.

The ossicular chain 37 includes three primary components: a malleus 40, an incus 45, and a stapes 50. The malleus 40 includes manubrium and head portions. The manubrium of the malleus 40 attaches to the tympanic membrane 30. The head of the malleus 40 articulates with one end of the incus 45. The incus 45 normally couples mechanical energy from the vibrating malleus 40 to the stapes 50. The stapes 50 includes a capitulum portion, comprising a head and a neck, connected to a footplate portion by means of a support crus comprising two crura. The stapes 50 is disposed in and against a membrane-covered opening on the cochlea 60. This membrane-covered opening between the cochlea 60 and middle ear 35 is referred to as the oval window 55. Oval window 55 is considered part of cochlea 60 in this patent application. The incus 45 articulates the capitulum of the stapes 50 to complete the mechanical transmission path.

Normally, prior to implantation of the invention, tympanic vibrations are mechanically conducted through the malleus 40, incus 45, and stapes 50, to the oval window 55. Vibrations at the oval window 55 are conducted into the fluid-filled cochlea 60. These mechanical vibrations generate fluidic motion, thereby transmitting hydraulic energy within the cochlea 60. Pressures generated in the cochlea 60 by fluidic motion are accommodated by a second membrane-covered opening on the cochlea 60. This second membrane-covered opening between the cochlea 60 and middle ear 35 is referred to as the round window 65. Round window 65 is considered part of cochlea 60 in this patent application. Receptor cells in the cochlea 60 translate the fluidic motion into neural impulses which are transmitted to the brain and perceived as sound. However, various disorders of the tympanic membrane 30, ossicular chain 37, and/or cochlea 60 can disrupt or impair normal hearing.

Hearing loss due to damage in the cochlea is referred to as sensorineural hearing loss. Hearing loss due to an inability to conduct mechanical vibrations through the middle ear is referred to as conductive hearing loss. Some patients have an ossicular chain 37 lacking sufficient resiliency to transmit mechanical vibrations between the tympanic membrane 30 and the oval window 55. As a result, fluidic motion in the cochlea 60 is attenuated. Thus, receptor cells in the cochlea 60 do not receive adequate mechanical stimulation. Damaged elements of ossicular chain 37 may also interrupt transmission of mechanical vibrations between the tympanic membrane 30 and the oval window 55.

Various techniques have been developed to remedy hearing loss resulting from conductive or sensorineural hearing disorder. For example, tympanoplasty is used to surgically reconstruct the tympanic membrane 30 and establish ossicular continuity from the tympanic membrane 30 to the oval window 55. Various passive mechanical prostheses and implantation techniques have been developed in connection with reconstructive surgery of the middle ear 35 for patients with damaged elements of ossicular chain 37. Two basic forms of prosthesis are available: total ossicular replacement prostheses (TORP), which is connected between the tympanic membrane 30 and the oval window 55; and partial ossicular replacement prostheses (PORP), which is positioned between the tympanic membrane 30 and the stapes 50.

Various types of hearing aids have been developed to compensate for hearing disorders. A conventional "air conduction" hearing aid is sometimes used to overcome hearing loss due to sensorineural cochlear damage or mild conductive impediments to the ossicular chain 37. Conventional hearing aids utilize a microphone, which transduces sound into an electrical signal. Amplification circuitry amplifies the electrical signal. A speaker transduces the amplified electrical signal into acoustic energy transmitted to the tympanic membrane 30. However, some of the transmitted acoustic energy is typically detected by the microphone, resulting in a feedback signal which degrades sound quality. Conventional hearing aids also often suffer from a significant amount of signal distortion.

Implantable hearing aid systems have also been developed, utilizing various approaches to compensate for hearing disorders. For example, cochlear implant techniques implement an inner ear hearing aid system. Cochlear implants electrically stimulate auditory nerve fibers within the cochlea 60. A typical cochlear implant system includes an external microphone, an external signal processor, and an external transmitter, as well as an implanted receiver and an implanted single channel or multichannel probe. A single channel probe has one electrode. A multichannel probe has an array of several electrodes. In the more advanced multichannel cochlear implant, a signal processor converts speech signals transduced by the microphone into a series of sequential electrical pulses corresponding to different frequency bands within a speech frequency spectrum. Electrical pulses corresponding to low frequency sounds are delivered to electrodes that are more apical in the cochlea 60. Electrical pulses corresponding to high frequency sounds are delivered to electrodes that are more basal in the cochlea 60. The nerve fibers stimulated by the electrodes of the cochlear implant probe transmit neural impulses to the brain, where these neural impulses are interpreted as sound.

Other inner ear hearing aid systems have been developed to aid patients without an intact tympanic membrane 30, upon which "air conduction" hearing aids depend. For example, temporal bone conduction hearing aid systems produce mechanical vibrations that are coupled to the cochlea 60 via a temporal bone in the skull. In such temporal bone conduction hearing aid systems, a vibrating element can be implemented percutaneously or subcutaneously.

A particularly interesting class of hearing aid systems includes those which are configured for disposition principally within the middle ear 35 space. In middle ear implantable (MEI) hearing aids, an electrical-to-mechanical output transducer couples mechanical vibrations to the ossicular chain 37, which is optionally interrupted to allow coupling of the mechanical vibrations to the ossicular chain 37. Both electromagnetic and piezoelectric output transducers have been used to effect the mechanical vibrations upon the ossicular chain 37.

One example of a partial middle ear implantable (P-MEI) hearing aid system having an electromagnetic output transducer comprises: an external microphone transducing sound into electrical signals; external amplification and modulation circuitry; and an external radio frequency (RF) transmitter for transdermal RF communication of an electrical signal. An implanted receiver detects and rectifies the transmitted signal, driving an implanted coil in constant current mode. A resulting magnetic field from the implanted drive coil vibrates an implanted magnet that is permanently affixed only to the incus 45. Such electromagnetic output transducers have relatively high power consumption requiring larger batteries, which limits their usefulness in total middle ear implantable (T-MEI) hearing aid systems.

A piezoelectric output transducer is also capable of effecting mechanical vibrations to the ossicular chain 37. An example of such a device is disclosed in U.S. Pat. No. 4,729,366, issued to D. W. Schaefer on Mar. 8, 1988. In the '366 patent, a mechanical-to-electrical piezoelectric input transducer is associated with the malleus 40, transducing mechanical energy into an electrical signal, which is amplified and further processed. A resulting electrical signal is provided to an electrical-to-mechanical piezoelectric output transducer that generates a mechanical vibration coupled to an element of the ossicular chain 37 or to the oval window 55 or round window 65. In the ’366 patent, the ossicular chain 37 is interrupted by removal of the incus 45. Removal of the incus 45 prevents the mechanical vibrations delivered by the piezoelectric output transducer from mechanically feeding back to the piezoelectric input transducer.

Figure 2:
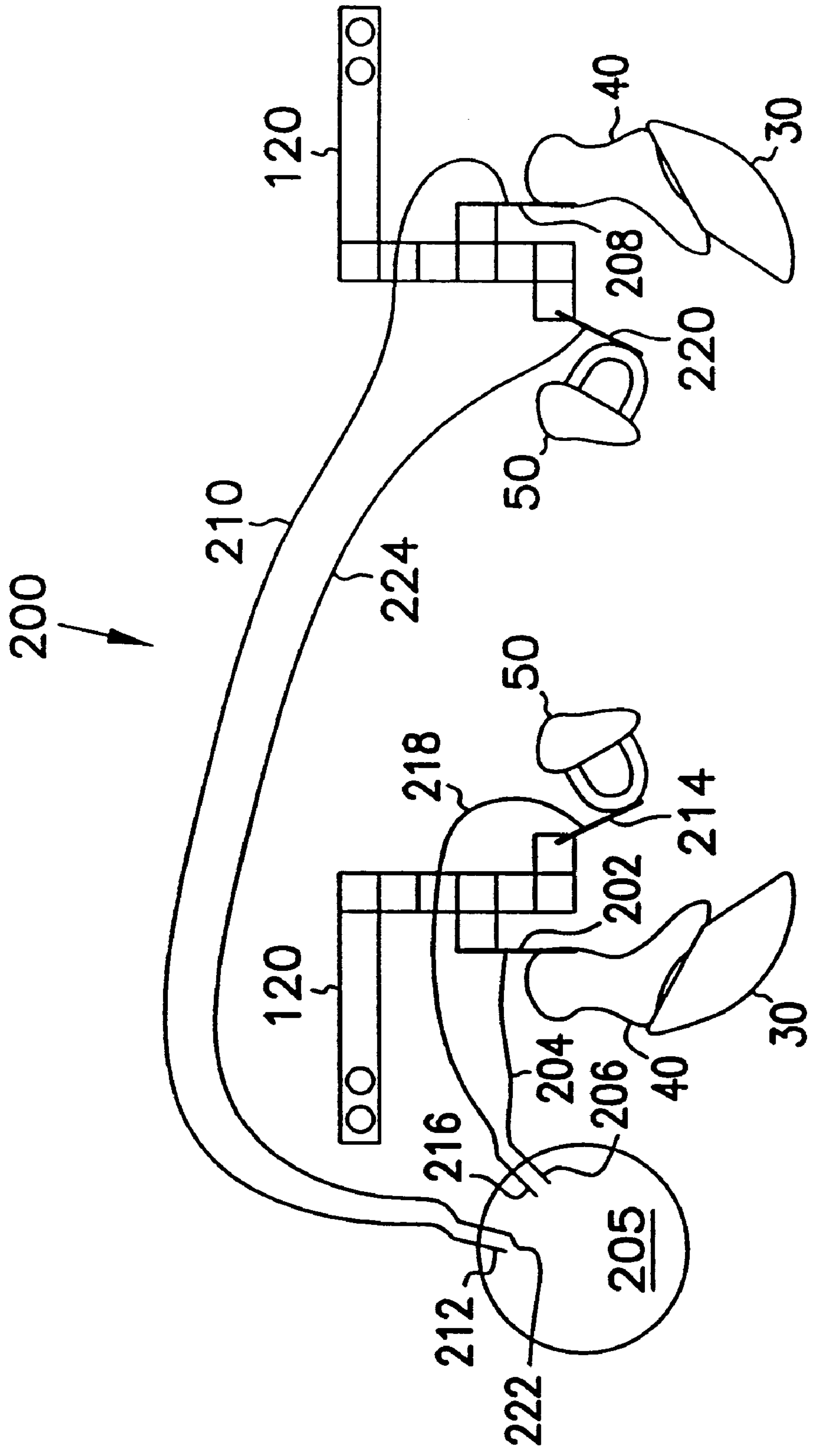
FIG. 2 is a schematic illustration of one embodiment of the invention for assisting hearing in both first and second ears using a dual path electronic device.

FIG. 2 illustrates schematically middle ear regions 35 of different first and second ears of a person, referred to as first and second middle ear regions, of a person implanted with a dual path hearing assistance system 200 according to one embodiment of the present invention. Dual path system 200 may be used instead of a single path system implanted in only one of the first and second middle ear regions. Dual path system 200 may alternatively be used instead of two single path systems that are each implanted in one of the first and second middle ear regions.

In FIG. 2, system 200 includes first-ear input transducer 202, which is mechanically coupled to malleus 40 of a first ear, such as the right ear, for receiving mechanical vibrations corresponding to sound. The mechanical vibrations are converted by transducer 202 into an electrical first-ear input signal that is electrically coupled through lead 204 to first-ear input 206 of an electronics unit or device 205.

System 200 also includes second-ear input transducer 208, which is mechanically coupled to malleus 40 of a second ear, such as the left ear, for receiving mechanical vibrations corresponding to sound. The mechanical vibrations are transduced by transducer 208 into an electrical second-ear input signal that is electrically coupled through lead 210 to second-ear input 212 of device 205.

System 200 also includes first-ear output transducer 214, which is electrically coupled through lead 218 to first-ear output 216 of device 205. Transducer 214 is mechanically coupled to cochlea 60 such as through stapes 50 of the first ear for providing mechanical vibrations corresponding to sound in response to an electrical first-ear output signal received from first-ear output 216 of device 205.

System 200 also includes second-ear output transducer 220, which is electrically coupled through lead 224 to second-ear output 222 of device 205. Transducer 220 is mechanically coupled to cochlea 60 such as through stapes 50 of the second ear for providing mechanical vibrations corresponding to sound in response to an electrical second-ear output signal received from second-ear output 222 of device 205.

System 200 provides, in the embodiment illustrated in FIG. 2, dual input signal paths and dual output signal paths. A first-ear input path includes lead 204 from transducer 202 to first-ear input 206 of device 205. A second-ear input path includes lead 210 from transducer 208 to second-ear input 212 of device 205. A first-ear output path includes lead 218 from device 205 to transducer 214. A second-ear output path includes lead 224 from device 205 to transducer 220.

Device 205 includes a signal processor which can process the input signals in different ways to produce the output signals. In one embodiment, the signal from each of the first-ear and second-ear input paths is separately processed in device 205, such as by amplification, filtering, or other signal processing, before being provided at the first-ear and second-ear outputs to the first-ear and second-ear output paths. In another embodiment, signals from the first-ear and second-ear input paths are combined, such as through weighted summing, during processing in device 205, before being provided to the first-ear and second-ear output paths. Variable parameters for the above-described processing in device 205 may be used to optimize signal processing, such as for each of the first and second ears.

Device 205 is implanted in the temporal bone of the skull, or at any other convenient location. For example, device 205 may be implanted in the temporal bone proximate to the first ear and leads 210 and 224 may be subcutaneously disposed along any convenient path between device 205 and the second ear.

Figure 3:
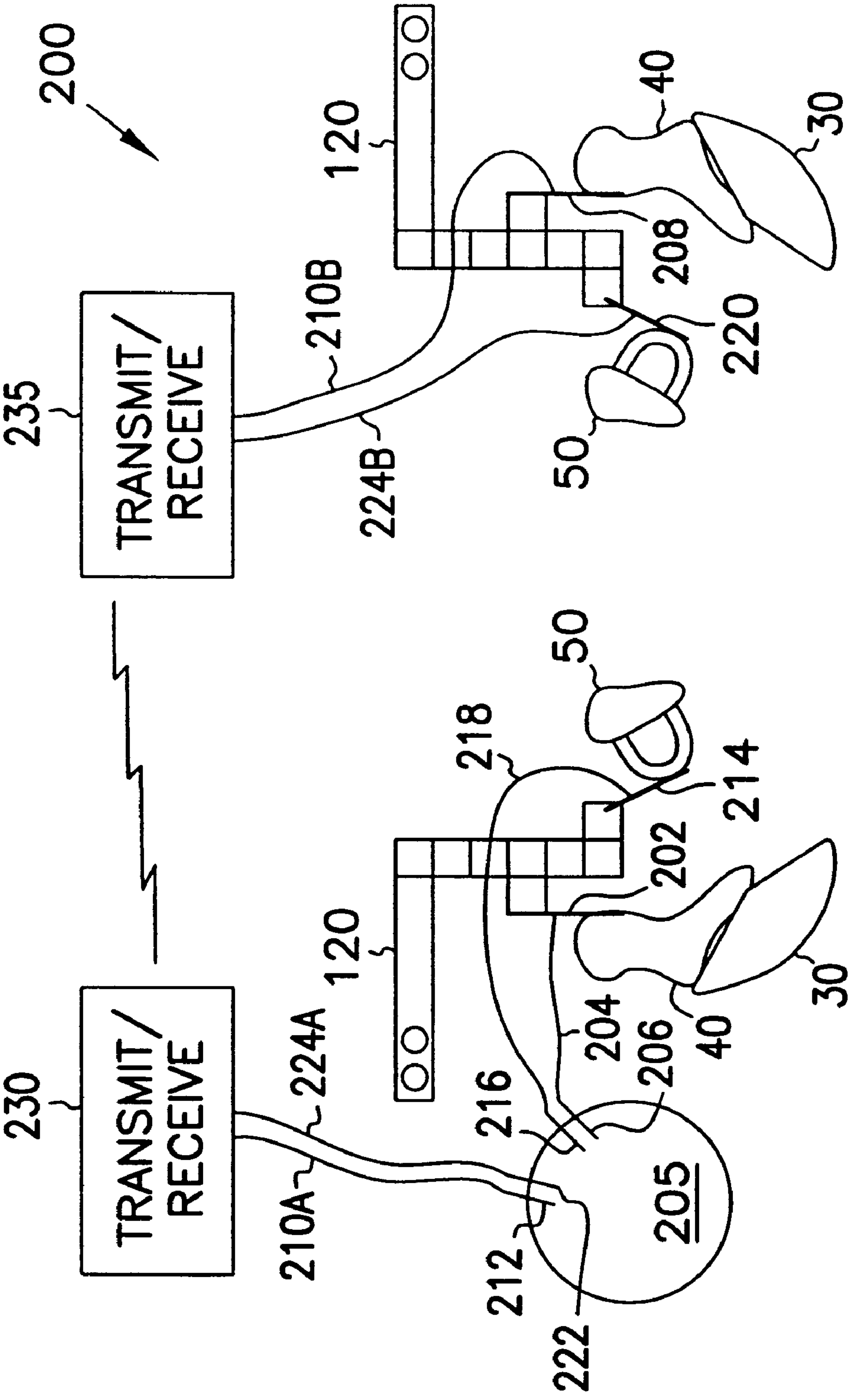
FIG. 3 is a schematic illustration of another embodiment of the invention using wireless communication between the electronic device and the second ear.

FIG. 3 illustrates generally another embodiment in which wireless communication is used between device 205 and the second ear, minimizing the need for subcutaneous disposition of leads 210 and 224. In FIG. 3, first transmitter/receiver 230 is electrically coupled to device 205. In this patent application, a transmitter/receiver is defined as any apparatus performing either electromagnetic transmission or reception, or both electromagnetic transmission and reception, or any other technique of wireless communication or sensing at a distance such as, for example, ultrasonic, infrasonic, and magnetoresistive techniques. Particular implementations could include amplitude modulation (AM), frequency modulation (FM), frequency-shift keying (FSK), phase-shift keying (PSK), pulse-width modulation (PWM), pulse-code modulation (PCM), or any other suitable communication scheme.

First transmitter/receiver 230 is preferably integrally contained within device 205, but first transmitter/receiver 230 may also be remotely disposed at any other convenient location. Second transmitter/receiver 235 is remotely disposed, either within the second ear, or implanted within the temporal bone proximate to the second ear, or at any other convenient location. Second transmitter/receiver 235 is electrically coupled to at least one, or both, of second input transducer 208 and second output transducer 220. First and second transmitter/receivers 230 and 235 are typically electromagnetically coupled for communication therebetween.

In FIG. 3, the second-ear input signal is provided by transducer 208 through lead 210B to second transmitter/receiver 235, electromagnetically coupled to first transmitter/receiver 230, and electrically coupled through lead 210A to device 205 for processing. Similarly, device 205 provides at second-ear output 222 the second-ear output signal, which is electrically coupled through lead 224A to first transmitter/receiver 230, electromagnetically coupled to second transmitter/receiver 235, and electrically coupled through lead 224B to transducer 220. A booster amplifier is optionally disposed together with either one of first transmitter/receiver 230 or second transmitter/receiver 235, or at any other convenient location, to provide amplification of the signals transmitted or received therefrom.

Dual path system 200 is particularly advantageous as an alternative to using a pair of single path systems, each implanted in one of the first and second ears. System 200 requires two procedures for separately implanting the various middle ear hardware in each ear, but it eliminates the need for a separate electronics unit or device associated with each hearing impaired ear. Thus, system 200 avoids implanting two separate electronics units; one electronics unit accommodates both of the first and second ears. Also, the present invention uses a battery disposed within the single electronics unit, device 205. Thus, battery replacement requires explantation of only a single device 205, thereby avoiding explantation of two separate electronics units.

Figure 4:
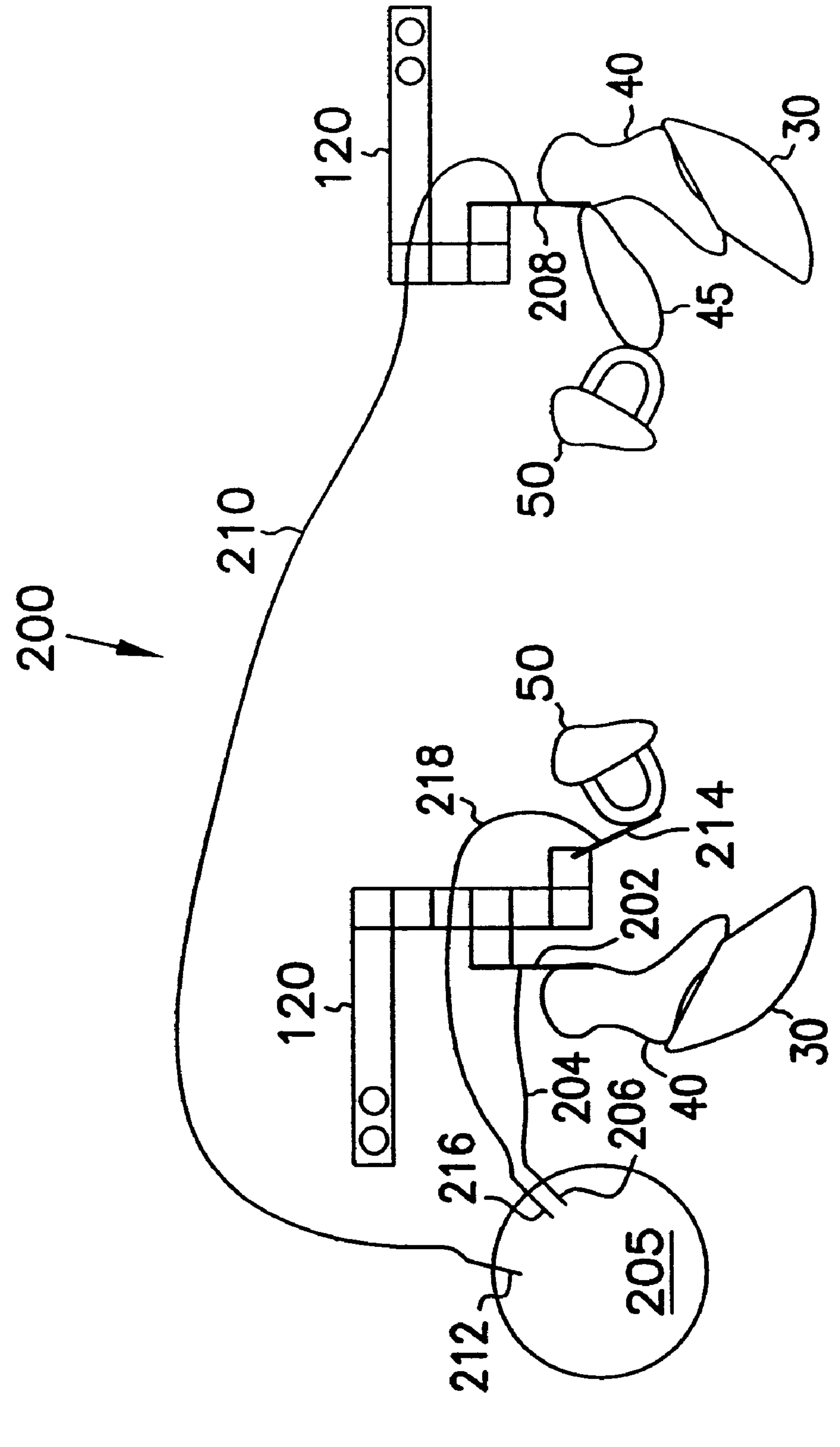
FIG. 4 is a schematic illustration of another embodiment of the invention including two input paths and one output path.

FIG. 4 illustrates another embodiment of the invention which is useful for a person having different degrees of hearing loss in each ear. FIG. 4 illustrates, by way of example, use of system 200 for profound sensorineural hearing loss in the second ear, but moderate to severe hearing loss in the first ear. In FIG. 4, input transducers 202 and 208 are each mechanically coupled to their respective malleus 40 bones and electrically coupled through respective leads 204 and 210 to device 205. The second ear, having profound sensorineural hearing loss, does not benefit from vibration of its stapes. In this example, no output transducer need be associated with the stapes of the second ear. Thus, only first-ear output transducer 214 is used. First-ear output transducer 214 is mechanically coupled to the stapes of the first ear and electrically coupled through lead 218 to first-ear input 216 of device 205.

In FIG. 4, transducers 202 and 208 transduce sound vibrations within middle ear portions of respective first and second ears into respective electrical first-ear and second-ear input signals, which are provided through respective first-ear and second-ear input paths to device 205. Device 205 performs signal processing, as described above, including the combining of signals received along the first-ear and second-ear input signal paths. A resulting electrical first-ear output signal is provided to transducer 214 to vibrate the stapes in the first ear and thereby stimulate the corresponding cochlea. This embodiment advantageously transduces and processes sound vibrations received at each side of the person's head, providing a resulting mechanical stimulation in that ear which does not have profound sensorineural hearing loss. This eliminates the "blind spot" which would occur using a conventional single input path system.

Figure 5:
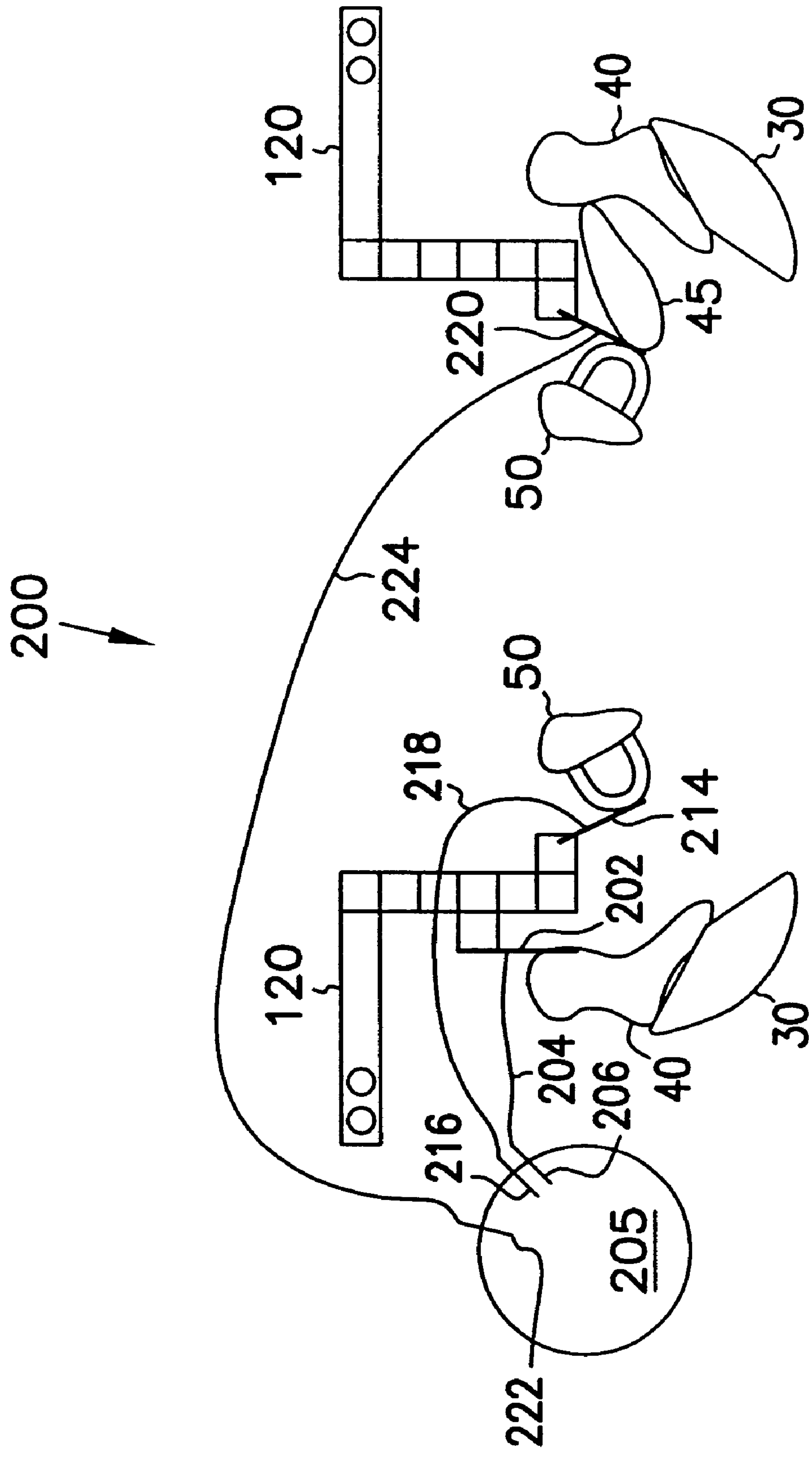
FIG. 5 is a schematic illustration of another embodiment of the invention including one input path and two output paths.

FIG. 5 illustrates, by way of example, an additional embodiment of the invention useful for a person having severe conductive hearing loss, such as chronic otitis media or post-tympanomastoidectomy, in the second ear and moderate to severe conductive or sensorineural hearing loss in the first ear. In FIG. 5, the invention uses both of the first-ear and second-ear output paths, but only one of the first-ear and second-ear input paths, such as the first-ear input path.

In FIG. 5, sound vibrations received by transducer 202 are transduced into an electrical first-ear input signal and electrically coupled via lead 204 to first-ear input 206 of device 205. Device 205 processes the first-ear input signal and provides resulting first-ear and second-ear output signals at first-ear and second-ear outputs 216 and 222 to each of the first-ear and second-ear output paths. The first-ear output signal at first-ear output 216 is electrically coupled through lead 218 to first-ear output transducer 214. The second-ear output signal at second-ear output 222 is electrically coupled through lead 224 to second-ear output transducer 220.

In one embodiment, substantially identical first-ear and second-ear output signals are provided at respective first-ear and second-ear outputs 216 and 222. In another embodiment, device 205 provides first-ear and second-ear output signals of different signal characteristics, with each of the first-ear and second-ear output signals tailored to meet the needs of the particular ear in which its associated output transducer is disposed. Processing parameters of device 205 may also be programmably adjusted to vary the signal characteristics of one or both of the first-ear and second-ear output signals such that the source or location of origin of the sound may be identified to a degree. Thus, this embodiment provides hearing assistance in both ears though the sound is actually only received from one ear.

Figure 6:
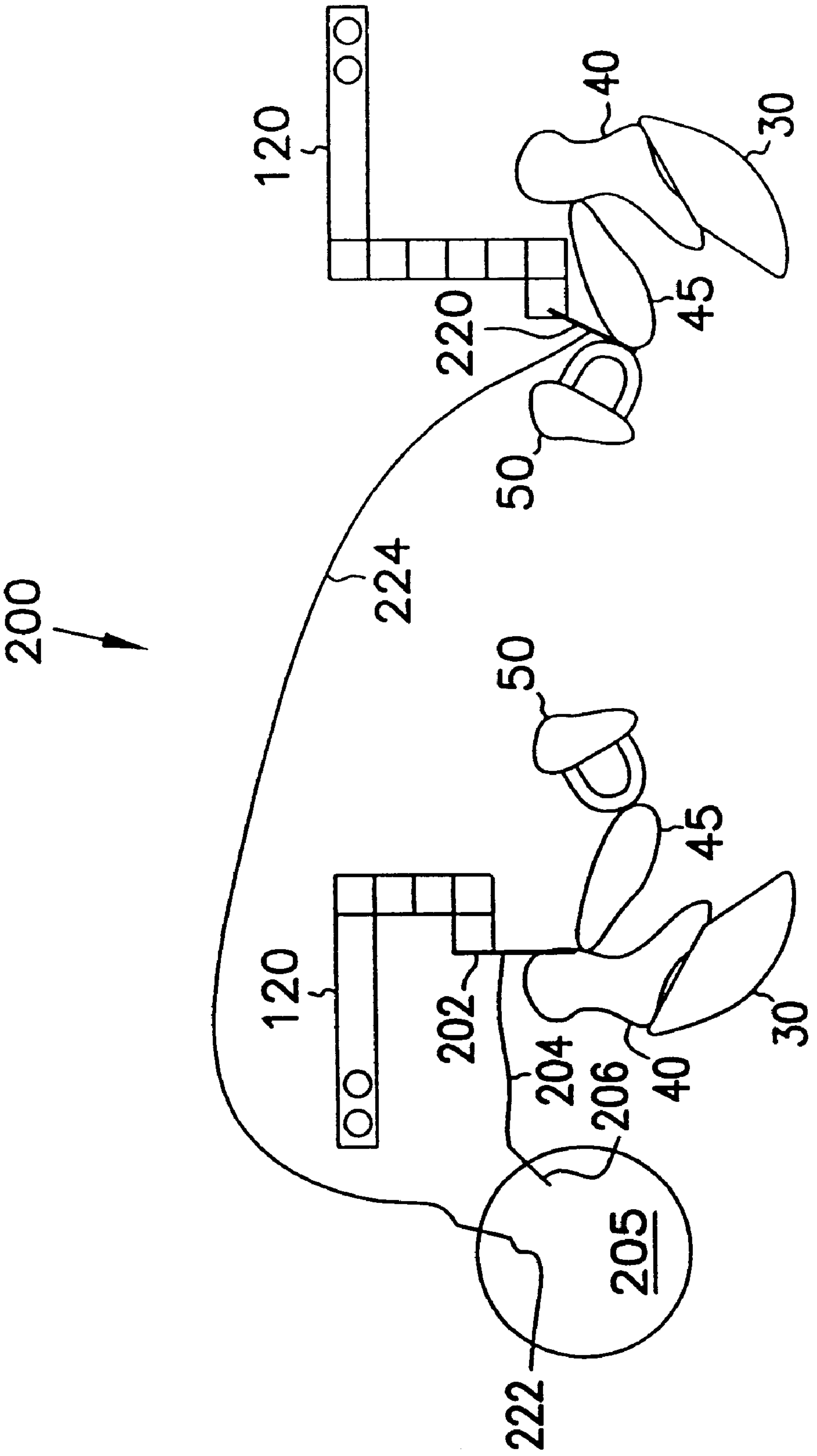
FIG. 6 is a schematic illustration of another embodiment of the invention including one input path corresponding to a first ear, and one output path corresponding to a second ear.

FIG. 6 illustrates an embodiment of the invention which provides a first-ear input path and a second-ear output path. In FIG. 6, sound vibrations received by transducer 202 are transduced into an electrical first-ear input signal and electrically couple via lead 204 to first-ear input 206 of device 205. Device 205 processes the first ear input signal and provides a resulting second-ear output signal at second-ear output 222 to the second-ear output path. The second-ear output signal at second-ear output 222 is electrically coupled through lead 224 to second-ear output transduer 220, which transduces the second-ear output signal into a mechanical output vibration that is mechanically coupled to stapes 50 of the second ear.

FIGS. 4–6 also illustrate leaving the incus 45 in place in those ears in which both an input transducer and an output transducer are not disposed, since mechanical feedback is typically not a problem unless both input and output transducers are disposed within the same ear. However, incus 45 may still be optionally removed for other reasons, such as ease of implementations. It is also understood that, when incus 45 is left in place, the corresponding input transducers may be mechanically coupled to the incus 45, rather than malleus 40, so as incorporate the particular frequency characteristics of the incudomalleolar joint between malleus 40 and incus 45. When the incus 45 is left in place, the corresponding output transducers may be coupled to the incus 45, and mechanical vibrations coupled to stapes 50 through incus 45. The input and output transducers may also be otherwise mechanically coupled within middle ear 35, including to prosthetic elements implanted therein.

Thus, invention provides an at least partially middle ear implantable dual path electronic hearing assist system 200 and method of use in both of a person's ears. The invention includes components for implantation within the middle ear regions of each ear, and provides: dual input paths; or, dual output paths; or, both dual input paths an dual output paths; or, a single input path corresponding to a first ear and a single output path corresponding to a second ear. The system is capable of use as a partial middle ear implantable (P-MEI) hearing aid system or a total middle ear implantable (T-MEI) hearing aid system.

What is claimed is:

1. A hearing assist system at least partially implantable in a middle ear, the system comprising:

a first-ear input transducer, proportioned for disposition within a first ear of a person, for transducing received mechanical sound vibrations within the first ear into an electrical first-ear input signal;

a second-ear output transducer, proportioned for disposition within a second ear of the person, for transducing an electrical second-ear output signal into mechanical sound vibrations within the second ear; and an electronics unit electrically coupled to the first-ear input transducer for receiving and processing the first-ear input signal, and electrically coupled to the second-ear output transducer for providing the electrical second-ear output signal.

2. The system of claim 1, wherein the first-ear input transducer is mechanically coupled to a malleus bone of the first ear and the second-ear output transducer is mechanically coupled to a stapes bone of the second ear.

3. The system of claim 1, further comprising a second-ear input transducer, proportioned for disposition within the second ear of the person, for transducing received mechanical sound vibrations within the second ear into an electrical second-ear input signal, and wherein the electronics unit is electrically coupled to the second-ear input transducer for receiving and processing the second-ear input signal.

4. The system of claim 3, wherein the second-ear input transducer is mechanically coupled to a malleus bone of the second ear.

5. The system of claim 3, wherein the first-ear output signal is produced from each of the first-ear and second-ear input signals by the electronics unit.

6. The system of claim 1, further comprising a first-ear output transducer, proportioned for disposition within the first ear of the person, for transducing an electrical first-ear output signal into mechanical sound vibrations within the first ear, and wherein the electronics unit is electrically coupled for providing the first-ear output signal to the first-ear output transducer.

7. The system of claim 6, wherein the first-ear output transducer is mechanically coupled to a stapes bone of the first ear.

8. The system of claim 6, wherein the electrical first-ear and second-ear output signals are produced from the first-ear input signal by the electronics unit.

9. The system of claim 6, wherein the electrical first-ear and second-ear output signals are produced from the second-ear input signal by the electronics unit.

10. A hearing assist system at least partially implantable in a middle ear, the system comprising:

a first-ear input transducer disposed within a first ear of a person for transducing received mechanical sound vibrations within the first ear into a corresponding electrical first-ear input signal;

a second-ear input transducer disposed within a second ear of the person for transducing received mechanical sound vibrations within the second ear into a corresponding electrical second-ear input signal;

a first-ear output transducer disposed within the first ear for transducing an electrical first-ear output signal into mechanical sound vibrations;

a second-ear output transducer disposed within the second ear for transducing an electrical second-ear output signal into mechanical sound vibrations;

an electronic device having first-ear and second-ear inputs for receiving respective electrical first-ear and second-ear input signals, and capable of processing the electrical first-ear and second-ear input signals and providing resulting respective first-ear and second-ear output signals at first-ear and second-ear outputs to the first-ear and second-ear output transducers, said communication of each of the second-ear input and output signals between the device and respective second-ear input and output transducers includes wireless communication.

11. The system of claim 10, further comprising:

a first transmitter/receiver, electrically coupled to each of the second-ear input and second-ear outputs of the device; and a second transmitter/receiver electrically coupled to each of the second-ear input and second-ear output transducers, and electromagnetically coupled to the first transmitter/receiver.

12. A dual path implantable hearing assistance device adapted to be implantable in a middle ear, the device comprising:

a first-ear input transducer adapted for installation in a middle ear section of a patient's first-ear;

a second-ear output transducer adapted for installation in a middle ear section of a patient's second-ear; and an electronics unit in electromagnetic communication with the first-ear input transducer and the second-ear output transducer, wherein, a first-ear input signal is provided by the first-ear input transducer, the first-ear input signal is processed by the electronics unit into a second-ear output signal, and the second-ear output signal is provided to the output transducer.

13. The device of claim 12, further comprising:

a second-ear input transducer adapted for installation in a second middle ear;

means for transmitting a second-ear input signal from the second-ear input transducer to the electronics unit in response to sound vibrations in the second-ear; and means for processing the second-ear input signal by the electronics unit into a second-ear output signal.

14. The device of claim 13, further comprising:

a first-ear output transducer adapted for installation in the first middle ear; and means for transmitting a first-ear output signal from the electronics unit to the first-ear output transducer, thereby producing auditory vibrations in the first middle ear.

15. The device of claim 14, further comprising means for transmitting the first-ear output signal in response to the first-ear input signal.

16. The device of claim 14, further comprising means for transmitting the second-ear output signal in response to the second-ear input signal.

17. The device of claim 14, wherein at least one of said means for transmitting the first-ear output signal and means for transmitting the second-ear output signal is in response to a combination of the first-ear and second-ear input signals.

18. The device of claim 14, wherein at least one of said means for transmitting the first-ear output signals and means for transmitting the second-ear output signals is in response to a weighted sum of the first-ear and second-ear input signals.

19. The device of claim 14, wherein the electronics unit is electrically coupled to each of the first-ear input and output transducers.

20. The device of claim 19, further comprising a first transmitter/receiver electrically coupled to the electronics unit and a second transmitter/receiver electrically coupled to at least one of the second-ear input transducer and the second-ear output transducer, wherein at least one of said second-ear input transducer and said second-ear output transducer is in wireless communication with the receiver/transmitter.

21. The device of claim 14, wherein said first-ear output signal transmitting means is carried out in a device electrically coupled to the first-ear input transducer.

22. The device of claim 21, further comprising means for wireless communication between a first transmitter/receiver electrically coupled to the device and a second transmitter/receiver electrically coupled to at least one of the second-ear input or output transducers, wherein the second-ear input signal is received and the second-ear output signal is provided.

* * * * *